(12) United States Patent
Parajuli et al.

(10) Patent No.: US 12,188,645 B2
(45) Date of Patent: Jan. 7, 2025

(54) HANDLE ASSEMBLY FOR ACCESSORY OF MEDICAL DEVICE SUPPORT SYSTEM

(71) Applicant: American Sterilizer Company, Mentor, OH (US)

(72) Inventors: Purushottam Parajuli, Solon, OH (US); Michael Hollopeter, Kirtland, OH (US); Steven H. Rus, Chardon, OH (US)

(73) Assignee: American Sterilizer Company, Mentor, OH (US)

( * ) Notice: Subject to any disclaimer, the term of this patent is extended or adjusted under 35 U.S.C. 154(b) by 62 days.

(21) Appl. No.: 18/329,935

(22) Filed: Jun. 6, 2023

(65) Prior Publication Data
US 2023/0408074 A1    Dec. 21, 2023

Related U.S. Application Data

(60) Provisional application No. 63/352,383, filed on Jun. 15, 2022.

(51) Int. Cl.
*F21V 21/40* (2006.01)
*A61B 90/35* (2016.01)
(Continued)

(52) U.S. Cl.
CPC .............. *F21V 21/40* (2013.01); *A61B 90/35* (2016.02); *F21V 23/0485* (2013.01);
(Continued)

(58) Field of Classification Search
CPC .......... F21W 2131/205; F21W 2131/20; F21W 131/205; F21V 21/403; F21V 23/04; F21Y 115/10
See application file for complete search history.

(56) References Cited

U.S. PATENT DOCUMENTS 11,039,899 B2    6/2021  Hollopeter et al.
2017/0112587 A1*  4/2017  Weiser .................. F21V 21/403
(Continued)

OTHER PUBLICATIONS

International Search Report for corresponding International Application No. PCT/US2023/024523 mailed Aug. 29, 2023.
(Continued)

*Primary Examiner* — William J Carter
(74) *Attorney, Agent, or Firm* — Renner, Otto, Boisselle & Sklar, LLP

(57) ABSTRACT

A handle assembly for an accessory of a medical device support system. The handle assembly includes a handle, an interface device, a conductive coating, and a connector. The interface device is in an outer surface of a generally tubular section of a handle housing of the handle and is configured to receive an input or transmit an output associated with the medical device support system. The conductive coating is on the inner surface of the generally tubular section and is configured to transmit one or more of power, ground, control signals, and communication signals corresponding to the input or the output of the interface device. The connector is connected to the conductive coating and is configured to transmit the one or more of the power, ground, control signals, and communication signals from the conductive coating to another part of the accessory and/or the medical device support system.

14 Claims, 13 Drawing Sheets

(51) Int. Cl.
 *F21V 23/04* (2006.01)
 *F21W 131/205* (2006.01)
 *F21Y 115/10* (2016.01)
 *A61B 90/30* (2016.01)

(52) U.S. Cl.
 CPC ... *A61B 2090/308* (2016.02); *A61B 2090/309* (2016.02); *F21W 2131/205* (2013.01); *F21Y 2115/10* (2016.08)

(56) References Cited

U.S. PATENT DOCUMENTS

| | | |
|---|---|---|
| 2018/0209623 A1* | 7/2018 | Strölin ................. A61B 90/361 |
| 2019/0214203 A1 | 7/2019 | Sanders et al. |
| 2020/0100860 A1 | 4/2020 | Hollopeter et al. |
| 2020/0177182 A1 | 6/2020 | Alexanderson et al. |

OTHER PUBLICATIONS

Written Opinion for corresponding International Application No. PCT/US2023/024523 mailed Aug. 29, 2023.

* cited by examiner

HANDLE ASSEMBLY FOR ACCESSORY OF MEDICAL DEVICE SUPPORT SYSTEM

This application claims priority to U.S. Patent Application No. 63/352,383, filed Jun. 15, 2022, which is hereby incorporated herein by reference in its entirety.

FIELD OF THE INVENTION

The technology of the present disclosure relates generally to a handle assembly for an accessory of a medical device support system, and more specifically to a handle assembly that includes a conductive coating, and a method of making same.

BACKGROUND

Accessories of medical device support systems typically include a handle to enable surgical personnel or other healthcare professionals to adjust the position of the accessory according to the needs of a specific medical procedure. One such medical device support system is a surgical lighting suspension system that includes one or more accessory light heads to illuminate a region of interest, for example a surgical treatment site or other medical site, below or proximate to the light head. The accessory light head typically includes a housing, one or more light emitting elements mounted inside the housing, and a handle assembly mounted to the housing to enable a healthcare professional or other individual to adjust the position of the light head. The handle is formed to have an ergonomic structure that enables a user to wrap a hand around the handle.

For handle assemblies of some medical device support systems there remain various shortcomings, drawbacks, and disadvantages relative to certain applications. For example, current handle assemblies may incorporate features such as pushbutton control elements, illuminated features, and/or cameras that require dedicated physical wiring harnesses within the housing of the handle. Owing to the tight space within the housing handle, achieving an ergonomic design with such features is difficult and makes the assembly process complicated and prone to failure. Increasing the size of the handle housing is undesirable and, in some cases, unacceptable in a medical setting. Moreover, cleaning pushbutton control elements on the external surface of the handle can be difficult.

Accordingly, there remains a need for further contributions in this area of technology.

SUMMARY OF INVENTION

The present disclosure relates to a handle assembly for an accessory of a medical device support system, and more specifically to a handle assembly that includes a conductive coating, and a method of making same.

According to one aspect of the invention, a handle assembly for an accessory of a medical device support system includes a handle including a handle housing made of an electrically insulating material, the handle having a sufficient size to be gripped by the human hand, the handle housing including a proximal end, a distal end, and a generally tubular section defining an interior region along a longitudinal axis, wherein the generally tubular section has an outer surface and an inner surface; an interface device in the outer surface of the generally tubular section that is configured to receive an input or transmit an output associated with the medical device support system; at least one conductive coating on the inner surface of the generally tubular section that is configured to transmit one or more of power, ground, control signals, and communication signals corresponding to the input or the output of the interface device; and, a connector connected to the at least one conductive coating and configured to transmit the one or more of the power, ground, control signals, and communication signals from the at least one conductive coating to another part of the accessory and/or the medical device support system.

Embodiments of the invention may include one or more of the following additional features separately or in combination.

The interface device may include a pushbutton in the outer surface and the at least one conductive coating may include a positive voltage trace and a button sense trace electrically connected to the pushbutton.

The interface device may include a plurality of pushbuttons in the outer surface and the at least one conductive coating may include a positive voltage trace and a button sense trace electrically connected to the pushbuttons in parallel.

The interface device may include a light emitting diode (LED) in the outer surface and the at least one conductive coating may include an LED+ drive trace and an LED− return trace electrically connected to the LED.

The interface device may include a plurality of light emitting diodes (LEDs) in the outer surface and the at least one conductive coating may include an LED+ drive trace and an LED− return trace electrically connected to the LEDs in parallel.

The at least one conductive coating may include a conductive pad and the interface device may include a capacitive touch interface section that are configured such that when the capacitive touch interface section is touched by the human hand a capacitor is formed by the human hand at the capacitive touch interface section, the conductive pad and the electrically insulating material of the handle housing there between.

The handle assembly may further include a capacitance detection circuit configured to detect a change in capacitance in the capacitor when the human hand touches the capacitive touch interface section.

The at least one conductive coating may include a conductive trace extending from the conductive pad to the connector, and the connector may be configured to transmit the change in capacitance to the capacitance detection circuit.

The capacitive touch interface section may include a printed silkscreen in the form of indicia associated with the accessory and/or the medical device support system.

The at least one conductive coating may include a capacitor electrode and the interface device may include a capacitive sensor interface section that are configured such that when the human body is within a predetermined distance to the capacitive sensor interface section a capacitor is formed by the human body within the predetermined distance to the capacitive sensor interface section, the capacitor electrode and the electrically insulating material of the handle housing there between.

The capacitor may be configured such that the capacitance in the capacitor increases as the human body approaches the capacitive sensor interface section.

The handle assembly may further include a capacitance detection circuit configured to detect the change in capacitance in the capacitor as the human body approaches the capacitive sensor interface section.

The at least one conductive coating may include a conductive trace extending from the capacitor electrode to the connector, and the connector may be configured to transmit the change in capacitance to the capacitance detection circuit.

According to another aspect of the invention, a method is provided for making a handle assembly for an accessory of a medical device support system, the method including providing a handle including a handle housing having a sufficient size to be gripped by the human hand, the handle housing including a proximal end, a distal end, and a generally tubular section defining a cavity along a longitudinal axis, wherein the generally tubular section has an outer surface and an inner surface; providing an interface device in the outer surface of the generally tubular section that is configured to receive an input or transmit an output associated with the medical device support system; depositing at least one conductive coating on the inner surface of the generally tubular section that is configured to transmit one or more of power, ground, control signals, and communication signals corresponding to the input or the output of the interface device; and, connecting a connector to the at least one conductive coating such that the connector is configured to transmit the one or more of the power, ground, control signals, and communication signals from the at least one conductive coating to another part of the accessory and/or the medical device support system.

These and further features will be apparent with reference to the following description and attached drawings which set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings. The invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

BRIEF DESCRIPTION OF THE DRAWINGS

The annexed drawings, which are not necessarily to scale, show various aspects of the present disclosure.

DETAILED DESCRIPTION

Figure 1:
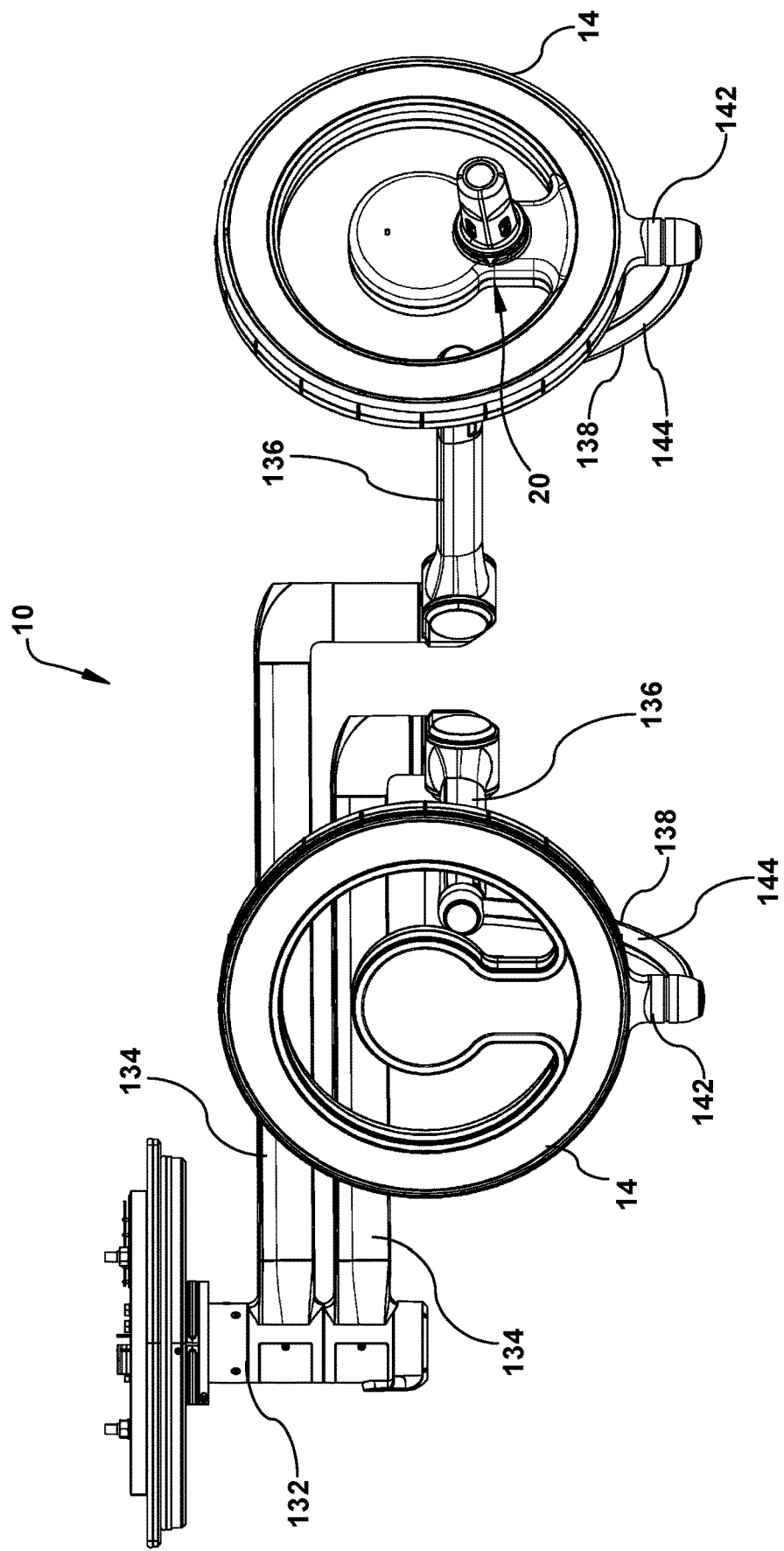
FIG. 1 is a side elevation view of an overall configuration of a medical device support system, showing a top of a left positioned accessory light head and a bottom of a right positioned accessory light head, each of which includes a handle assembly in accordance with an embodiment of the invention.

For the purpose of promoting an understanding of the principles of the present disclosure, reference will now be made to the embodiments illustrated in the drawings and specific language will be used to describe the same. It will nevertheless be understood that no limitation of the scope of the present disclosure is thereby intended. The Figures are not necessarily to scale. Features that are described and/or illustrated with respect to one embodiment may be used in the same way or in a similar way in one or more other embodiments and/or in combination with or instead of the features of the other embodiments. Any alterations and further modifications of the described embodiments, and any further applications of the principles of the present disclosure as described herein, are contemplated as would normally occur to one skilled in the art to which the present disclosure relates.

FIGS. 1-7 show a handle assembly 20 for an accessory 14 of a medical device support system 10 in accordance with an embodiment of the invention. The handle assembly 20 includes a handle 30 including a handle housing 32 made of an electrically insulating material and having a sufficient size to be gripped by the human hand. The handle housing 32 includes a proximal end 40, a distal end 42, and a generally tubular section 44 defining an interior region 50 along a longitudinal axis L-L, wherein the generally tubular section 44 has an outer surface 60 and an inner surface 62. An interface device 70 is provided in the outer surface 60 of the generally tubular section 44 that is configured to receive an input and/or transmit an output associated with the medical device support system 10. At least one conductive coating 90 is provided on the inner surface 62 of the generally tubular section 44 that is configured to transmit one or more of power, ground, control signals, and communication signals corresponding to the input or the output of the interface device 70. A connector 122 is connected to conductive coating 90 and is configured to transmit the one or more of the power, ground, control signals, and communication signals from conductive coating 90 to another part of the accessory 14 and/or the medical device support system 10.

As will be described in greater detail below, several advantages may be realized by the components of the handle assembly 20 in accordance with the invention. For example, the handle assembly 20 eliminates the need for, or at least reduces the volumetric footprint of, a dedicated physical wiring harness for providing power, ground and/or signals to LEDs, pushbuttons, and/or any sensors residing in or on the handle housing 32 of the handle 30. This not only simplifies the design and assembly process but also reduces costs and improves reliability. In some embodiments, the integrated conductive coating 90 enables replacement of physical pushbuttons in the handle housing 32 with a capacitive touch functionality. This will improve cleanability of the handle housing 32. In some embodiments, conductive coating 90 enables integration of a capacitive proximity sensor functionality to allow the implementation of, for example, an encroachment indicator for the accessory 14.

Turning initially then to FIG. 1, an exemplary medical device support system 10 may be a surgical lighting suspension system 10 that includes two accessory light heads 14 each having a handle assembly 20. It will be appreciated that in other embodiments, the medical device support system 10 may comprise other types of support systems and may include accessories other than light heads 14, for example monitors and/or dedicated cameras. The medical device support system 10 includes a central shaft or support column 132 that is suspended from the ceiling, and two generally horizontal extension arms 134 mounted to the shaft 132 for rotational movement about the central shaft 132. In other implementations, the central shaft 132 could be mounted to a wall or stand rather than the ceiling. Two load balancing arms 136 are pivotably mounted to the distal ends of the respective extension arms 134. Yoke assemblies 138 are mounted to the distal ends of the respective load balancing arms 136. The yoke assemblies 138, in turn, support the respective accessory light heads 14 for multi-axis movement relative to the load balancing arms 136. Each accessory light head 14 includes a bushing or other coupling member 142 that rotatably connects the accessory light head 14 to the distal end of an arm 144 of a respective yoke assembly 138. Each accessory light head 14 includes a handle assembly 20 that enables a healthcare professional or other individual to adjust the position of the accessory light head 14 to a desired orientation relative to, for example, a patient operating table and healthcare professionals in the operating room.

Figure 2:
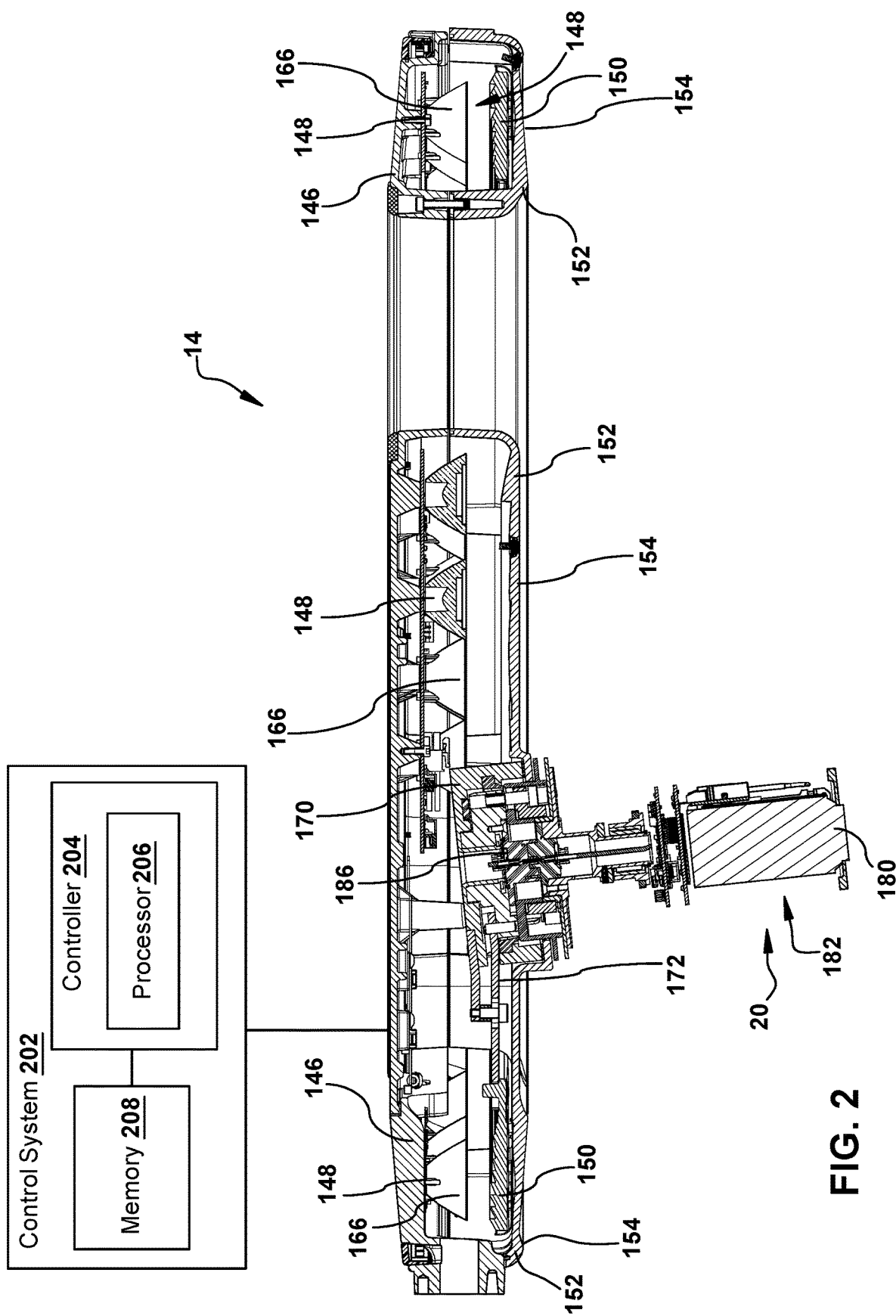
FIG. 2 is a side cross section view of an accessory light head, showing a housing base, a housing cover, and internal components of the accessory light head and the handle assembly thereof.

With additional reference to FIG. 2, each accessory light head 14 of the medical device support system 10 includes, in addition to a handle assembly 20, a housing base 146, a plurality of light emitting elements 148 such as light emitting diodes (LEDs), an annular shape lens 150, and a housing cover 152 including a housing lens 154. The annular shape lens 150 and the housing lens 154 are in a light emitting path of the plurality of light emitting elements 148. A plurality of collimators 166 may be provided in the light emitting paths of the respective plurality of light emitting elements 148. The handle assembly 20 is rotatably mounted coaxially to a hub 170 of the accessory light head 14. A lever 172 is provided for transferring rotational motion from the handle 30 of the handle assembly 20 to the annular shape lens 150. It will be appreciated that in other embodiments, the handle assembly 20 may be mounted in a stationary manner, although components within the handle housing 32, for example a later-described camera 180, may be configured to rotate therein. The annular shape lens 150, the housing lens 154, and the collimators 166, if provided, are configured such that rotation of the annular shape lens 150 relative to the housing lens 154 by the handle 30 spreads and/or bends the light emitted by the light emitting elements 148. The light emitting elements 118 of the accessory light head 14 emit light to a region of interest, for example a surgical treatment site or other medical site below or proximate the accessory light head 14.

The illustrated handle assembly 20 is equipped with the interface device and conductive coating 90 to be described in greater detail below, as well as a camera assembly 182, a pair of printed circuit boards (PCBs) 184, and a plug adapter 186. The camera assembly 182 is configured for rotation about the longitudinal axis L-L and to output an optical video signal pertaining to images and/or video of the region of interest captured by the camera 180. In some embodiments, the camera assembly 182 may be omitted. The PCBs 184 provide electronics for transmitting power, ground, control signals, and communication signals associated with the interface device 70 and the camera assembly 182. The connector 122 is mounted on the upper one of the pair of PCBs 184 and is connected to conductive pads 188 of conductive coating 90, for example, by a suitable board to wire connection or board to board connection. This connector-to-pad connection can be achieved, for example, through spring-loaded pins on the connector side and/or through a flat flex ribbon cable. The pins and/or cable, in turn, can be pressed into the conductive pads 188 of the conductive coating 90 for example, by brackets or by any two adjacent parts. The plug adapter 186 is configured to transmit power, ground, and signals between the handle assembly and the interior of the light head housing 146, 152, including the power, ground, and signals corresponding to the interface device 70, conductive coating and the camera assembly 182. The handle housing 32 has a sufficient size to be gripped by the human hand meaning that the outer diameter or outer perimeter of the handle housing 32 is selected to enable the human hand to be comfortably wrapped around the handle housing 32.

A control system 202 controls the operation of the components of the accessory light head 14 including the handle assembly 20 thereof. The control system 202 may include a controller 204 that is configured to carry out overall control of the functions and operations of the control system 202. The controller 204 may include a processor 206, such as a central processing unit (CPU), microcontroller, or microprocessor. The processor 206 executes code stored in a memory (not shown) within the controller 204 and/or in a separate memory, such as the memory 208, in order to carry out operation of the control system 202. Referring to FIG. 2, the control system 202 is located in the light head housing 146, 152 of the accessory light head 14. In other embodiments, the control system 202 may be located in the handle housing 32, or outside of the light head housing 146, 152, or even outside of the medical device support system 10. In still other embodiments, the control system 202 may be located in a combination of two or more of the light head housing 146, 152, the handle housing 32, outside of the light head housing 146, 152, and outside of the medical device support system 10.

With continued reference to FIG. 2, the control system 202 is configured control the light emitting elements 118 in emitting light to a region of interest. The control system 202 also is configured to receive the optical video signal from the camera assembly 182 to process data captured by the camera 180. As will be described in greater detail below, the control system 202 also is configured to process control signals and communication signals associated with the interface device 70 of the handle assembly 20.

Figure 3:
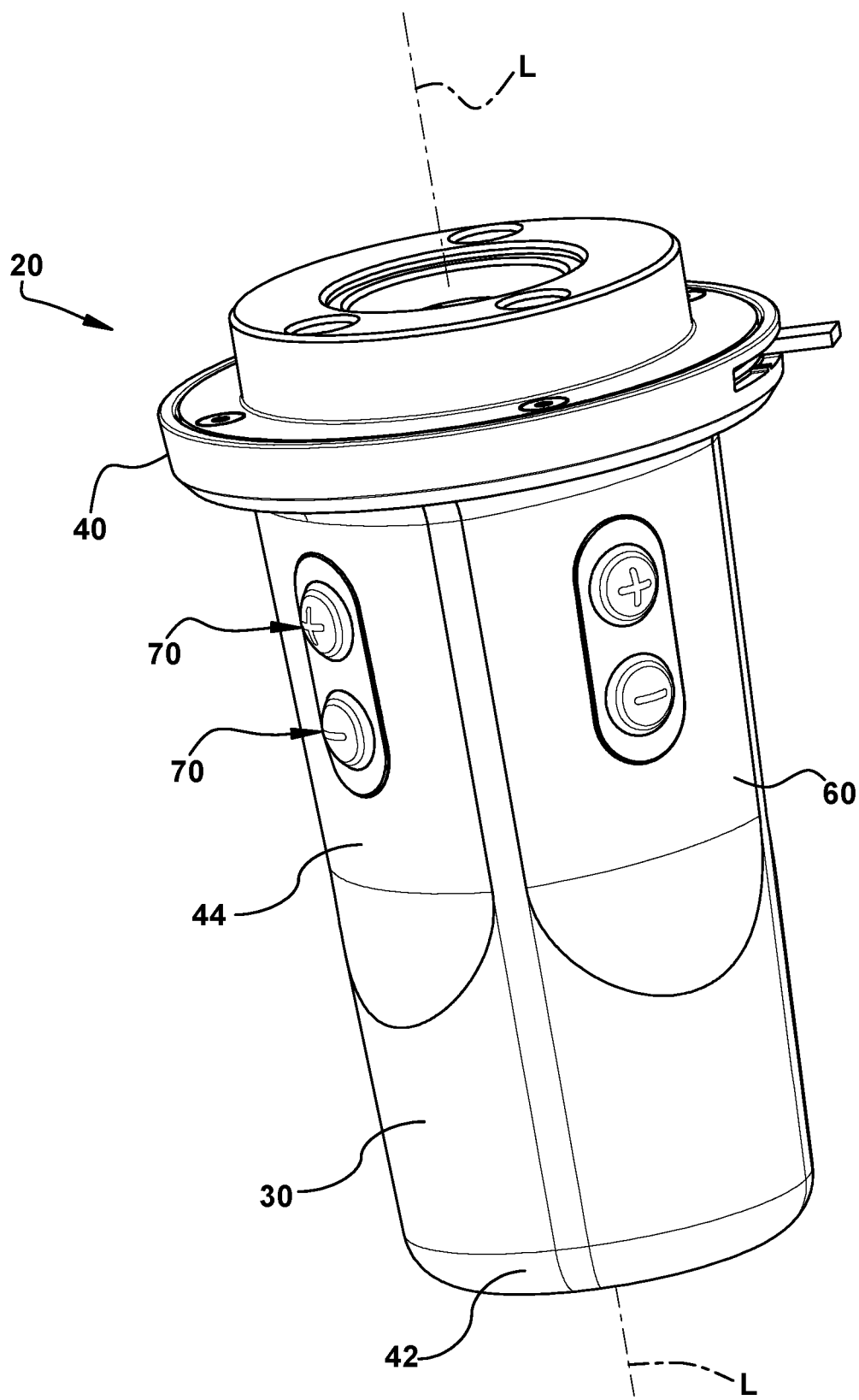
FIG. 3 is a perspective side view of a handle assembly in accordance with an embodiment of the present invention, the handle assembly including a pushbutton interface device and an LED interface device in accordance with an embodiment of the invention.
Figure 4:
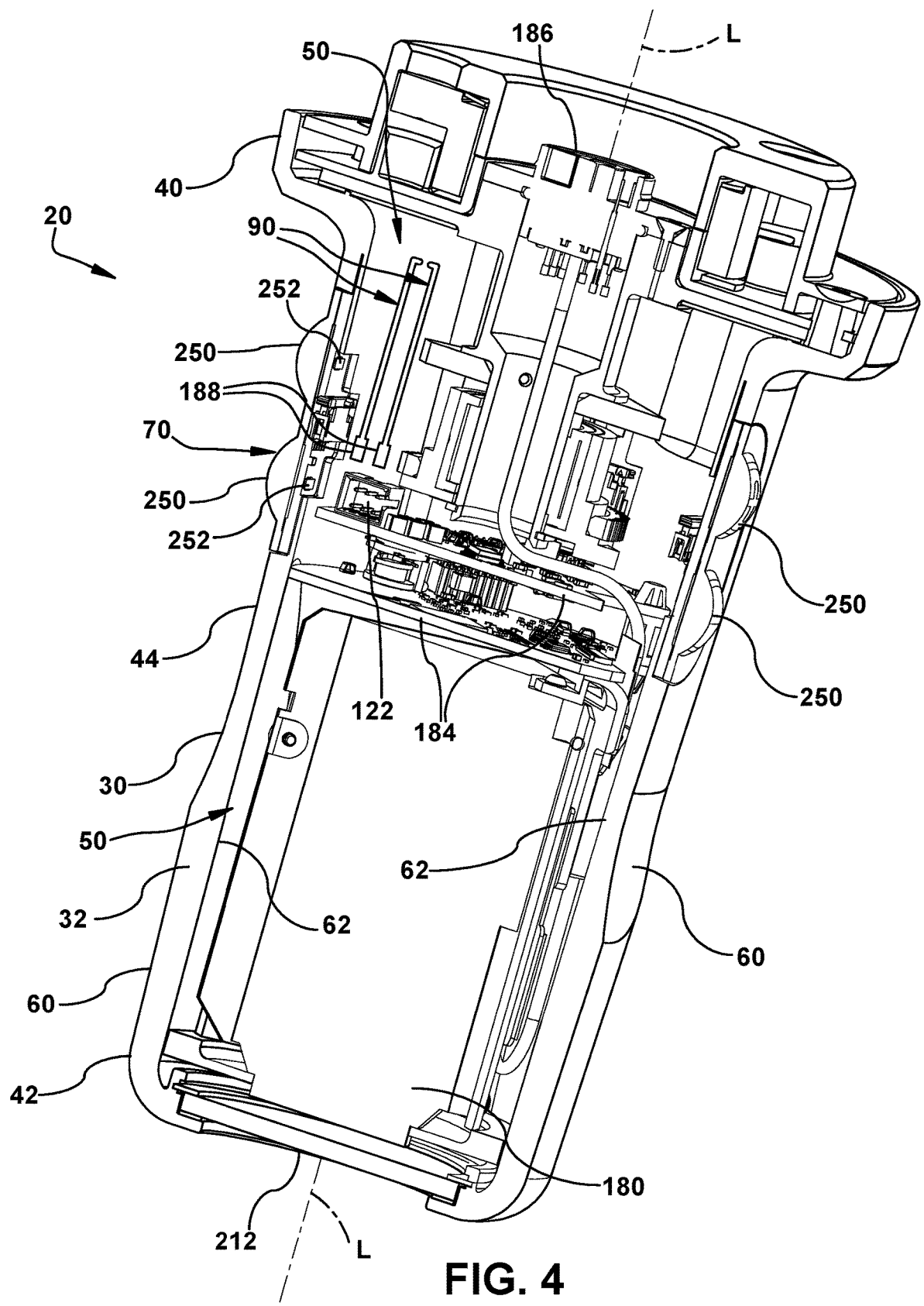
FIG. 4 is a perspective cross section view of the handle assembly of FIG. 3, showing internal components of the handle assembly.

FIGS. 3 and 4 show further details of the handle assembly 20 in accordance with an embodiment of the invention. The handle housing 32 of the handle assembly 20 is made of any one or more suitable electrically insulating materials including, for example, polypropylenes, polyesters, polycarbonates, polyimides, among others. The generally tubular section 44 of the handle housing 32 has a sufficient size to be gripped by the human hand. In some embodiments, the generally tubular section 44 may have a generally circular axial cross section, or a generally polygonal axial cross section with curved corners, or a combination of these in the axial direction of the handle housing 32. The outer axial cross section dimension, that is the outer diameter or outer perimeter, of the generally tubular section 44 may be tapered or otherwise change in the axial direction downward from the light head housing 146, 152. In some embodiments, the generally tubular section 44 may have a length along the longitudinal axis L-L in the range of about 5.3 inches to about 7.5 inches. The outer axial cross section dimension of the generally tubular section 44 may be in the range of about 1.25 inches to about 3.5 inches. The wall thickness of the generally tubular section 44 may be in the range of about 0.06 inch to about 0.2 inch. As shown in FIG. 4, the distal end 42 or bottom of the generally tubular section 44 may open downward to enable insertion of the camera 180 and/or other components therethrough, and a cap 212 may be provided to close the open bottom.

The handle assembly 20 includes first and second embodiments of an interface device 70 in the outer surface 60 of the generally tubular section 44 and corresponding first and second embodiments of a conductive coating 90 on the inner surface 62 of the generally tubular section 44. The first embodiment of the interface device 70 comprises a pushbutton 250 that is configured to control attributes of the emitted light from the accessory light head 14, for example, switching the accessory light head 14 on and off, adjusting the light intensity and/or color temperature of the light emitting elements 148, among other things. In some embodiments, a pushbutton 250 may also, or alternately, be provided to interface with a drive motor to rotate the camera assembly 182 within the handle housing 32, or to control the camera 180 to zoom in or zoom out relative to a target of interest.

The second embodiment of the interface device 70 comprises a light emitting diode (LED) 252. In the illustrated embodiment, the LED 252 is configured to illuminate the pushbutton 250 to enhance visibility of the pushbutton 250 under a dimmed lighting environment. The pushbutton 250 may be translucent to facilitate the passage of light therethrough emitted by the LED 252. In some embodiments, an LED 252 may also, or alternately, be provided to illuminate another portion of the handle assembly 20, for example, to indicate the camera assembly 182 is in an operating mode.

Figure 5:
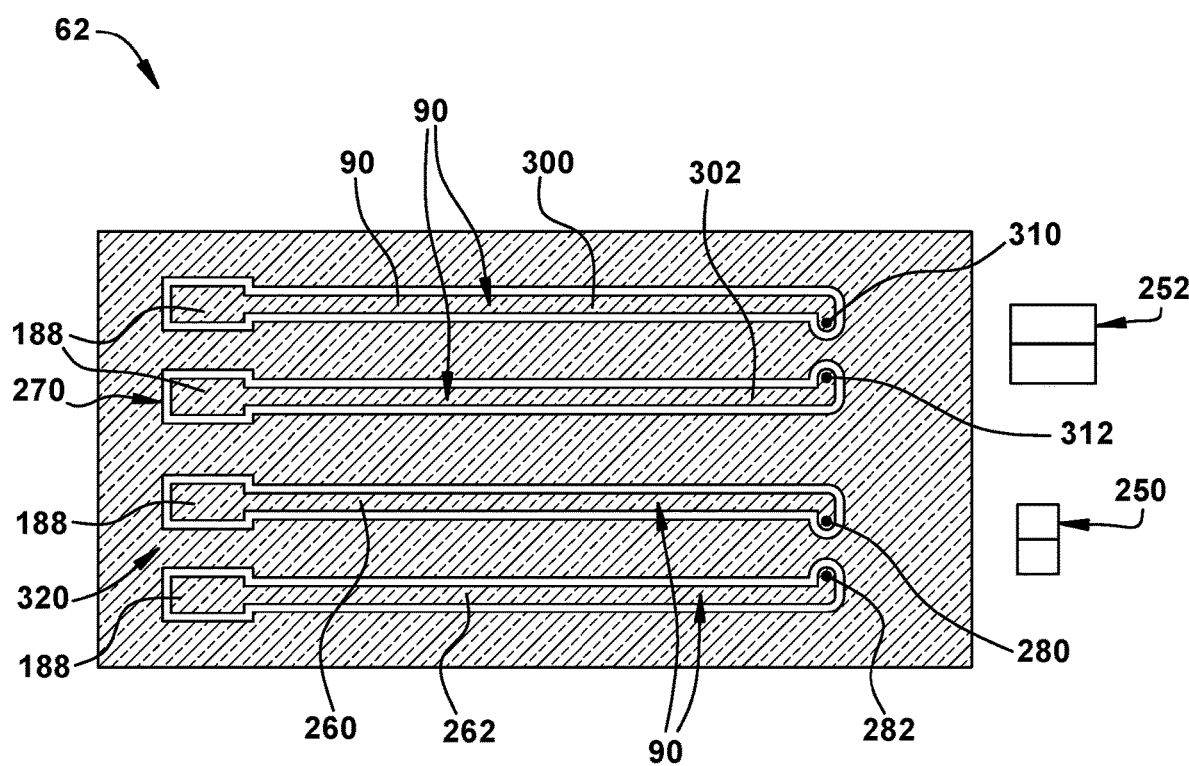
FIG. 5 is a schematic planar unfolded view of an inner surface of a generally tubular section of the handle assembly of FIG. 3, showing a conductive coating in accordance with an embodiment of the invention, including a positive voltage trace and a button sense trace for the pushbutton interface device, and an LED+ drive trace and an LED− return trace for the LED interface device.
Figure 6:
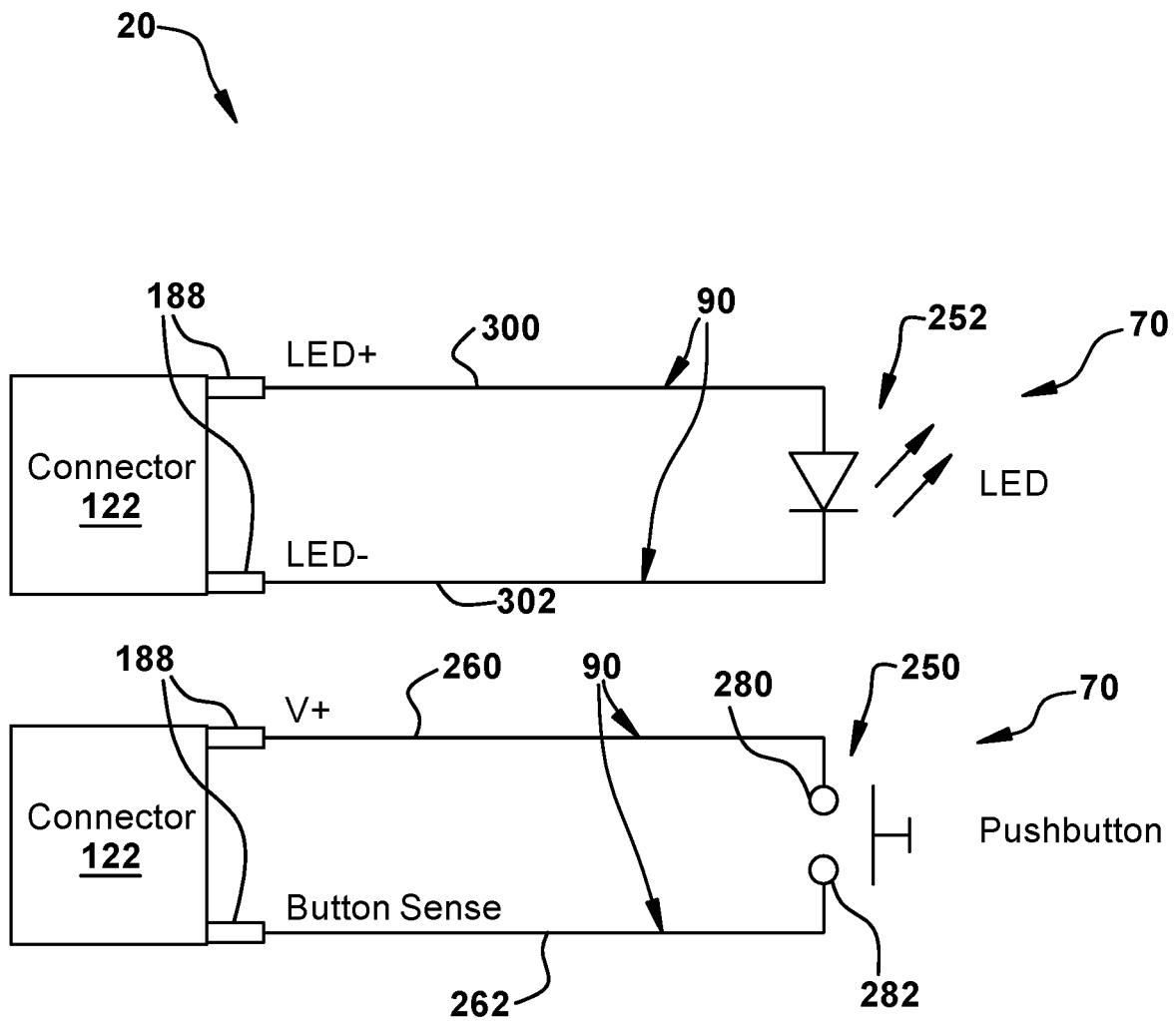
FIG. 6 is a circuit diagram schematic view of the pushbutton interface device and the LED interface device of FIG. 5, showing electrical connections to the pushbutton interface device and the LED interface device.

Turning now to FIGS. 5 and 6, the first and second embodiments of the corresponding conductive coatings 90 will now be described in greater detail. FIG. 5 shows in schematic planar unfolded view the inner surface 62 of the generally tubular section 44 of the handle housing 32 including an exemplary layout of conductive coating 90. FIG. 6 shows the corresponding circuit diagram of the embodiments of the interface device 70 and the corresponding conductive coating 90.

For the pushbutton 250, the corresponding conductive coating 90 includes a positive voltage trace 260 and a button sense trace 262 electrically connected to the pushbutton 250 (right side of FIG. 6). Conductive coating 90 may include metals such as copper, aluminum, nickel, silver, chromium, or alloys of these metals. Conductive coating 90 may be formed on the inner surface 62 of the generally tubular section 44 by any suitable conductive coating technique including, for example, painting, spraying, dispensing, electroplating, electroless plating, electromagnetic interference (EMI) coating techniques, or combinations of the foregoing. In one form, a conductive coating is deposited onto the inner surface 62 and subsequently the conductive coating 90 is selectively etched out of the deposited conductive coating, as shown for example by the etched away portions 270 in FIG. 5. In another form, portions not to be covered by conductive coating are masked off by a mask material and subsequently the conductive coating is applied. The mask may then be removed, leaving the desired conductive coating 90. Electrical contacts 280, 282 may be provided, for example by gluing, at respective ends of the traces 260, 262 to form a pushbutton circuit as shown schematically in FIG. 6. As will be appreciated, the positive voltage trace 260 and the button sense trace 262 are activated each time the pushbutton 250 is depressed. The positive voltage trace 260 and the button sense trace 262 terminate at the respective conductive pads 188 (left side of FIG. 5) that are connected to the afore described connector 122 of the handle assembly 20, which leads to the control system 202 residing in the light head housing 146, 152 or to another part of the medical device support system 10 as earlier described.

With continued reference to FIGS. 5 and 6, the second embodiment of the interface device 70 includes the LED 252 in the outer surface 60 of the generally tubular section 44 and the corresponding conductive coating 90 on the inner surface 60 of the generally tubular section 44. For the LED 252, the corresponding conductive coating 90 includes an LED+ drive trace 300 and an LED− return trace 302 electrically connected to the LED 252 (right side of FIG. 6), and respective conductive pads 188 (left side of FIG. 5) that are connected to the afore described connector 122 of the handle assembly 20. As with the traces 260, 262 of conductive coating 90 leading to the pushbutton 250, the traces 300, 302 of the conductive coating 90 leading to the LED 252 may include any suitable conductive coating material and may be formed by any suitable conductive coating technique. Electrical contacts 310, 312 may be provided, for example by gluing, at respective ends of the LED+ drive trace 300 and the LED− return trace 302 to form an LED circuit as shown schematically in FIG. 6. The LED+ drive trace 300 and the LED− return trace 302 terminate at the respective conductive pads 188 (left side of FIG. 5) that are connected to the afore described connector 122 of the handle assembly 20, which leads to the control system 202 residing in the light head housing 146, 152 or to another part of the medical device support system 10, as earlier described.

In some embodiments, an additional conductive coating 320 may be applied to portions of the inner surface 62 of the generally tubular section 44 that are spaced from conductive coating 90. The additional conductive coating 320 may be configured to shield the electronics of the handle assembly 20, for example the camera assembly 182, from electromagnetic interference (EMI). The additional conductive coating 320 may also, or alternately, be configured to prevent electromagnetic crosstalk within the handle assembly 20.

As will be appreciated, conductive coating 90 for an interface device 70 typically will include power and ground-return traces, as was described above with respect to the pushbutton 250 which is powered by the positive voltage trace 260 and the button sense trace 262, and the LED 252 which is powered by the LED+ drive trace 300 and the LED− return trace 302. For sensors on the handle housing 32, conductive coating 90 typically will include power and ground-return traces to power the sensor in addition to a signal trace to transmit a signal generated by the sensor. The sensor may be a distance sensor, for example, that generates a signal corresponding to a distance measured from the sensor to a target of interest. The signal trace, in turn, may transmit the signal to the control system 202 for processing.

Figure 7:
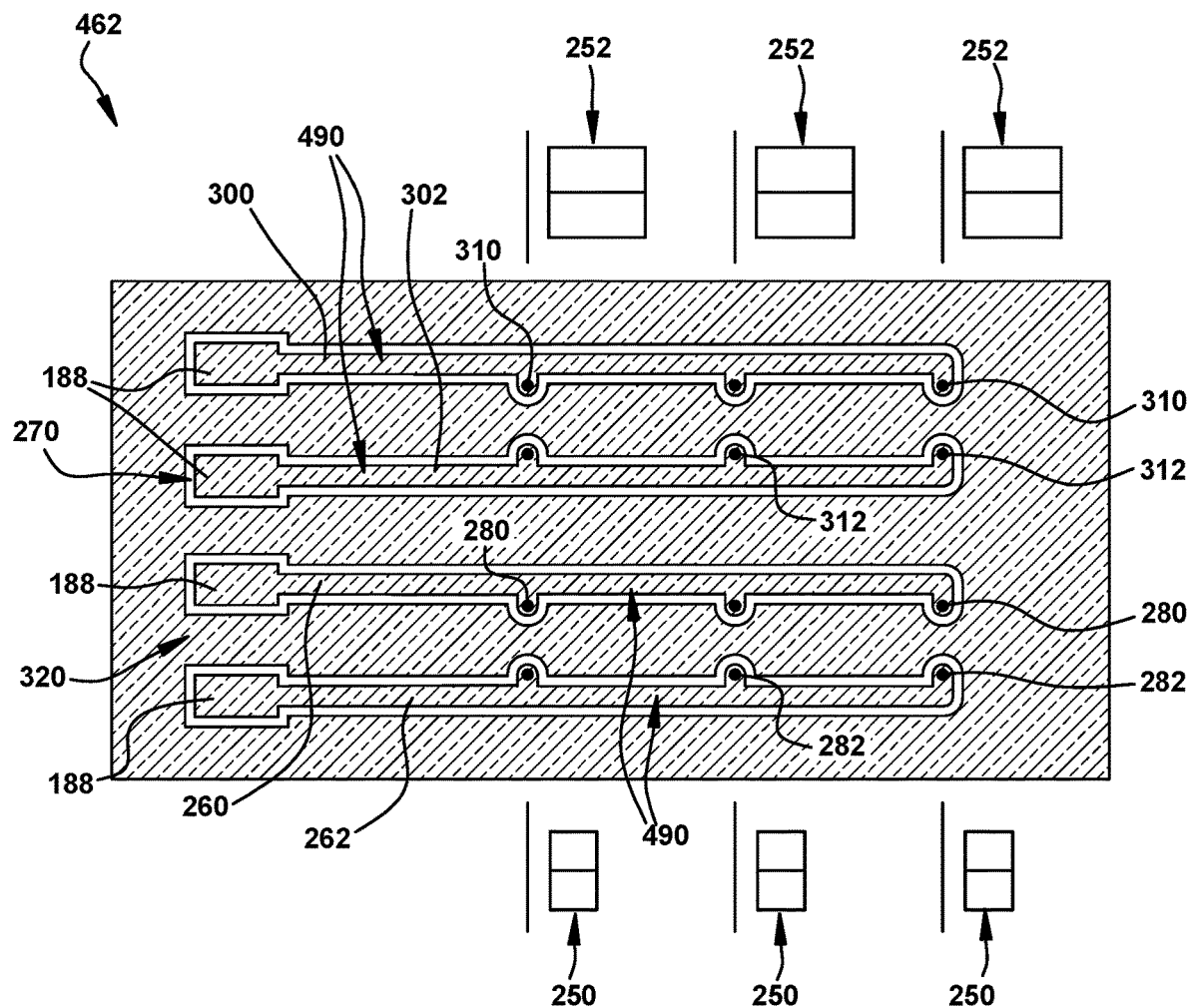
FIG. 7 is a schematic planar unfolded view of an inner surface of the generally tubular section of the handle assembly of FIG. 3, showing conductive coating in accordance with another embodiment of the invention, similar to the FIG. 5 embodiment except with traces that provide for plural pushbutton interface devices and plural LED interface devices.

Traces of conductive coating 90 can be expanded on the inner surface 62 of the generally tubular section 44 to different series and parallel combinations of interconnects as necessary or desired for an application before terminating to the connector 122. FIG. 7 shows such an application in accordance with an embodiment of the invention. The FIG. 7 inner surface 462 and conductive coating 490 is in many respects similar to the above-described inner surface 62 and conductive coating 90, and consequently the same reference numerals are used to denote structures corresponding to similar structures in the inner surface 62 and conductive coating 90. In addition, the foregoing description of the inner surface 62 and conductive coating 90, including the integration into the handle assembly 20, is equally applicable to the FIG. 7 inner surface 462 and conductive coating 490 except as noted below. Moreover, it will be appreciated upon reading and understanding the specification that aspects of the inner surfaces 62, 462 and conductive coatings 90, 490 may be substituted for one another or used in conjunction with one another where applicable.

In the FIG. 7 embodiment, and with additional reference to FIGS. 3, 4 and 6, the interface device 70 includes a plurality of pushbuttons 250 and a plurality of light emitting diodes (LEDs) 252 in the outer surface 60 of the generally tubular section 44. Conductive coating 490 on the inner surface 62 of the generally tubular section 44 includes a positive voltage trace 260 and a button sense trace 262 electrically connected to the pushbuttons 250 in parallel. Similarly, for the LEDs 252, conductive coating 490 includes an LED+ drive trace 300 and an LED− return trace 302 electrically connected to the LEDs 252 in parallel.

As will be appreciated, the use of conductive coatings 90 on the inner surface of the generally tubular section 44 of the handle housing 32 instead of a wiring harness within the handle housing 32 reduces the volumetric footprint required for integrating the pushbuttons 250, the LEDs 252, and/or any sensors residing in or on the handle housing 32 of the handle 30. This not only simplifies the design and assembly process but also reduces costs and improves reliability. For example, using conductive coatings 90 in place of wiring to power the pushbuttons 250 and LEDs 252 frees up space within the handle housing 32, which provides a wider path for installing or servicing the camera assembly 182 and more space for rotation of the camera assembly 182 about the longitudinal axis L-L during adjusting of the camera 180. Referring to the top of FIG. 4, it will be appreciated that the use of conductive coatings 90 in place of wiring also translates into less congestion within the handle housing 32, thereby improving access to the PCBs 184 or other electronics of the handle assembly 20 and reducing the possibility of wire entanglement and/or inadvertent snagging of electronics.

Figure 8:
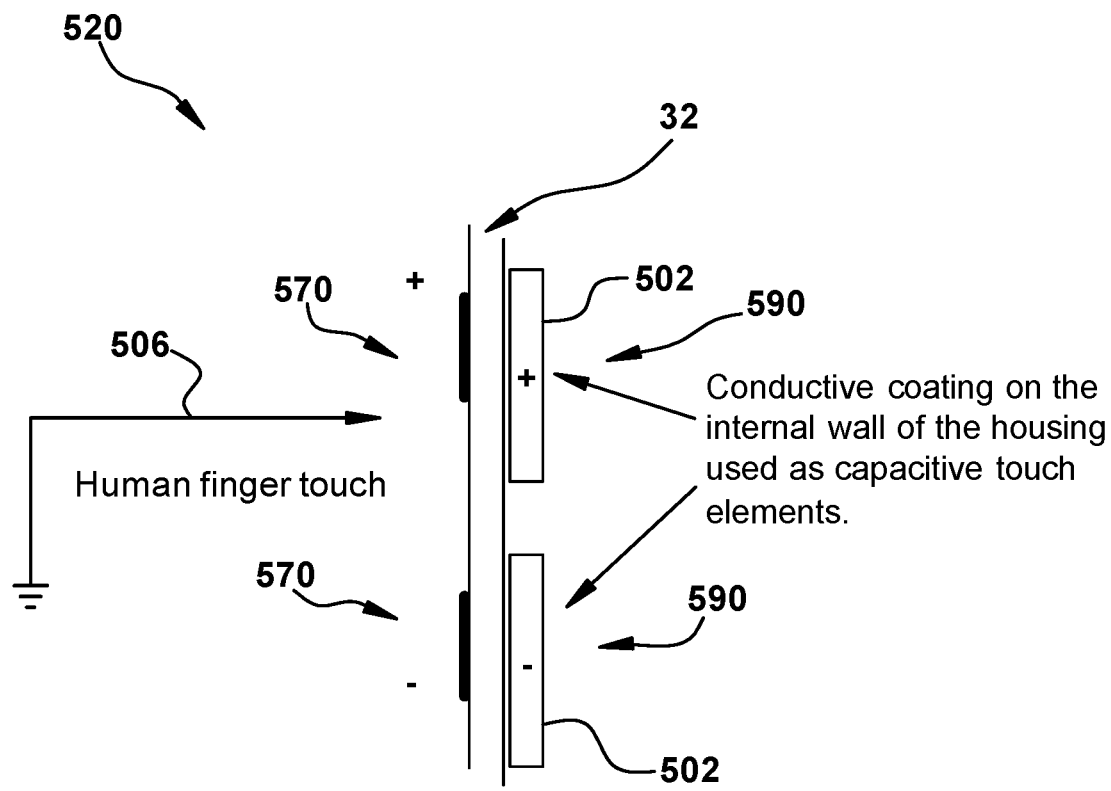
FIG. 8 is a side cross sectional view of a portion of a handle housing of a handle assembly in accordance with another embodiment of the invention, the portion of the handle housing being where an interface device in the form of a capacitive touch interface section and conductive coating in the form of a conductive pad and respective conductive trace are provided.
Figure 9:
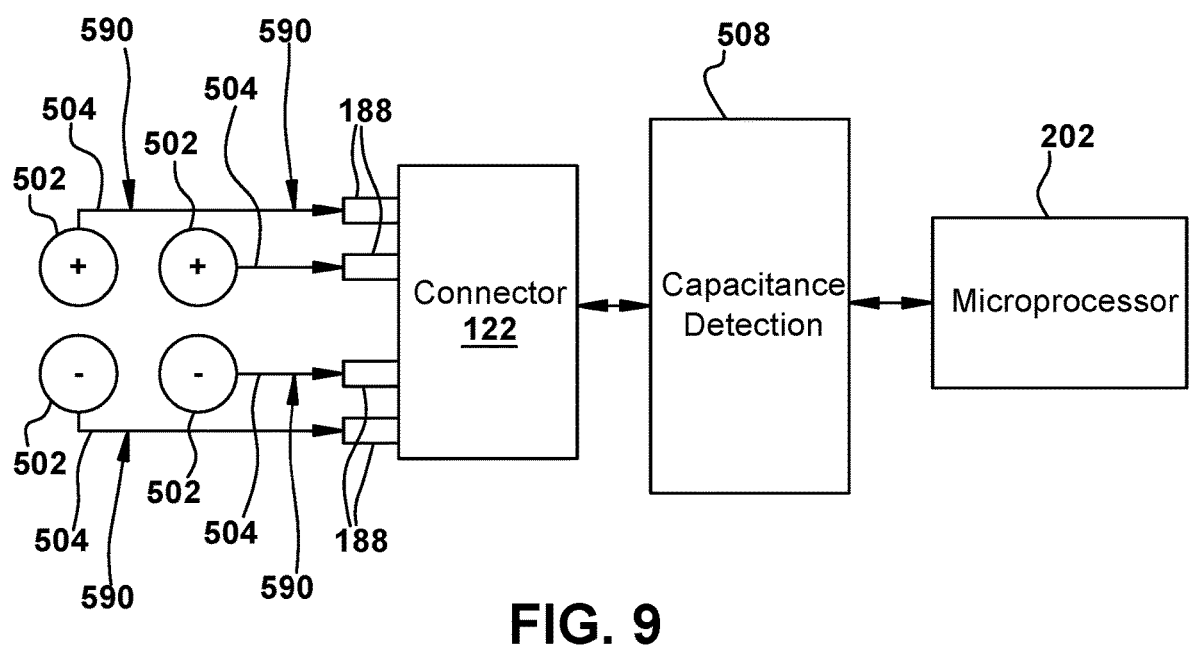
FIG. 9 is a schematic view showing the conductive coating of the FIG. 8 handle assembly and a capacitance detection circuit and a processor electrically connected to conductive coating.
Figure 10:
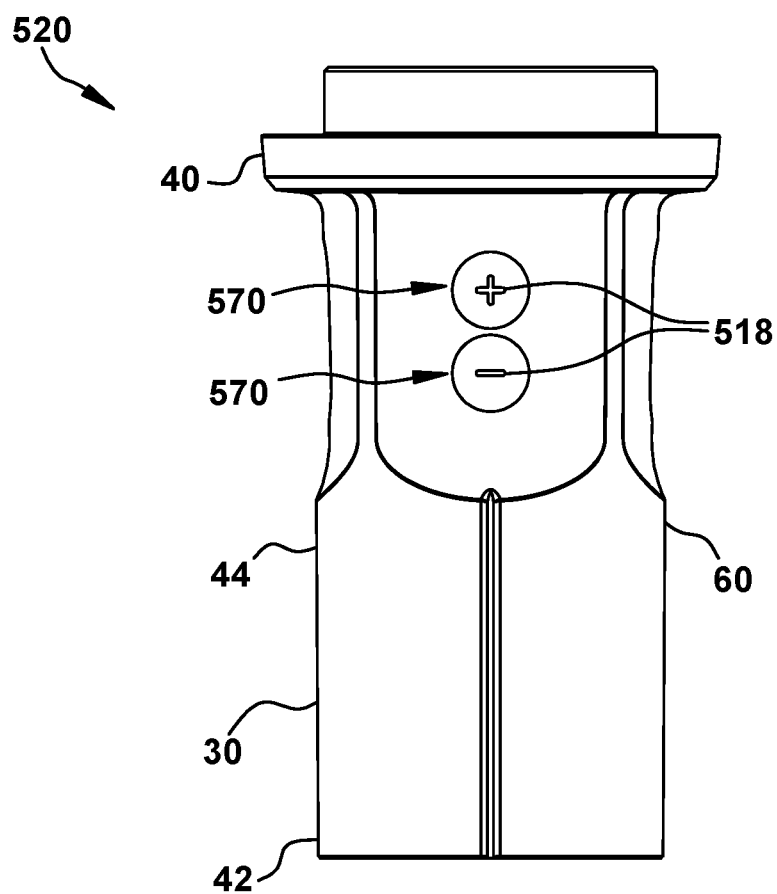
FIG. 10 is a side elevation view of the FIG. 8 handle assembly, showing capacitive touch interface sections in the outer surface of the generally tubular section of the handle housing including respective printed silkscreen buttons that correspond to respective conductive pads shown in FIG. 9.

FIGS. 8-10 show a handle assembly 520 in accordance with another embodiment of the invention. The FIGS. 8-10 handle assembly 520 is in many respects similar to the above-described handle assembly 20 of FIGS. 3-6, and consequently the same reference numerals are used to denote structures corresponding to similar structures in the handle assembly 20. In addition, the foregoing description of the FIGS. 3-6 handle assembly 20, including the integration into the accessory light head 14 and the medical device support system 10, is equally applicable to the FIGS. 8-10 handle assembly 520 except as noted below. Moreover, it will be appreciated upon reading and understanding the specification that aspects of the handle assemblies 20, 520 may be substituted for one another or used in conjunction with one another where applicable.

The handle assembly 520 includes an interface device 570 in the outer surface 60 of the generally tubular section 44 in the form of capacitive touch interface sections 570, and a conductive coating 590 on the inner surface 62 of the generally tubular section 44 in the form of different islands of conductive pads 502 and respective conductive traces 504. Each conductive pad 502, or island 502, of conductive coating 590 serves as a conductor to form a capacitive interface. More specifically, and with reference to FIG. 8, the human hand or finger 506 can be viewed as a ground electrode such that when a corresponding capacitive touch interface section 570 is touched by the human hand 506, a capacitor is formed by a combination of the human hand 506 at the capacitive touch interface section 570, the corresponding conductive pad 502, and the electrically insulating material of the handle housing 32 there between. As such, the touching of the handle 30 at a capacitive touch interface section 570, that is from above a corresponding conductive pad 502, results in a change in capacitance. As shown in FIG. 9, the corresponding conductive trace 504 of conductive coating 590 transmits the change in capacitance from the conductive pad 502 to the conductive pad 188 to which the connector 122 is connected. The connector 122, in turn, transmits the change in capacitance to a capacitance detection circuit 508 mounted on one of the PCBs 124 for example. The capacitance detection circuit 508 detects the change in capacitance and communicates the detection to the afore described control system 202 for processing. The capacitance detection circuit 508 may be implemented through commercially available integrated circuits (ICs).

FIG. 10 shows the outside of the handle assembly 520. As shown in FIG. 10, the capacitive touch interface sections 570 in the outer surface 60 of the generally tubular section 44 of the handle housing 30 may include printed silkscreen buttons 518 that correspond to the respective underlying conductive pads 502 shown in FIG. 9. The printed silkscreen buttons 518 may include indicia, for example plus sign (+) and minus sign (−) as shown, associated with the accessory light head 14, the handle assembly 520 thereof, and/or the medical device support system 10. Thus, for example, when the human hand 506 touches the plus sign (+) silk screen button 518, the change in capacitance in the capacitor (formed by the human hand 506, the handle housing 32, and the corresponding underlying conductive pad 502) is transferred to the connector 122 and control system 202, where the control system 202 may, for example, control the accessory light head 14 to increase the light intensity of the light emitting elements 148. Similarly, when the human hand 506 touches the minus sign (−) silk screen button 518, the change in capacitance in the capacitor is transferred to the connector 122 and control system 202, where the control system 202 may, for example, control the accessory light head 14 to decrease the light intensity of the light emitting elements 148. In some embodiments, the plus sign (+) silk screen button 518 and the minus sign (−) silk screen button 518 may be configured such that touching of same by the human hand 506 functions to control the camera 180 to respectively zoom in and zoom out relative to the target of interest.

As will be appreciated, the integration of conductive coating 590 into the inner surface 62 of the generally tubular section 44 of the handle housing 32 enables replacement of the physical pushbuttons 250 with a capacitive touch functionality. In addition to the afore mentioned benefits of providing additional space within the handle housing 32, this will improve cleanability of the handle housing 32.

Figure 11:
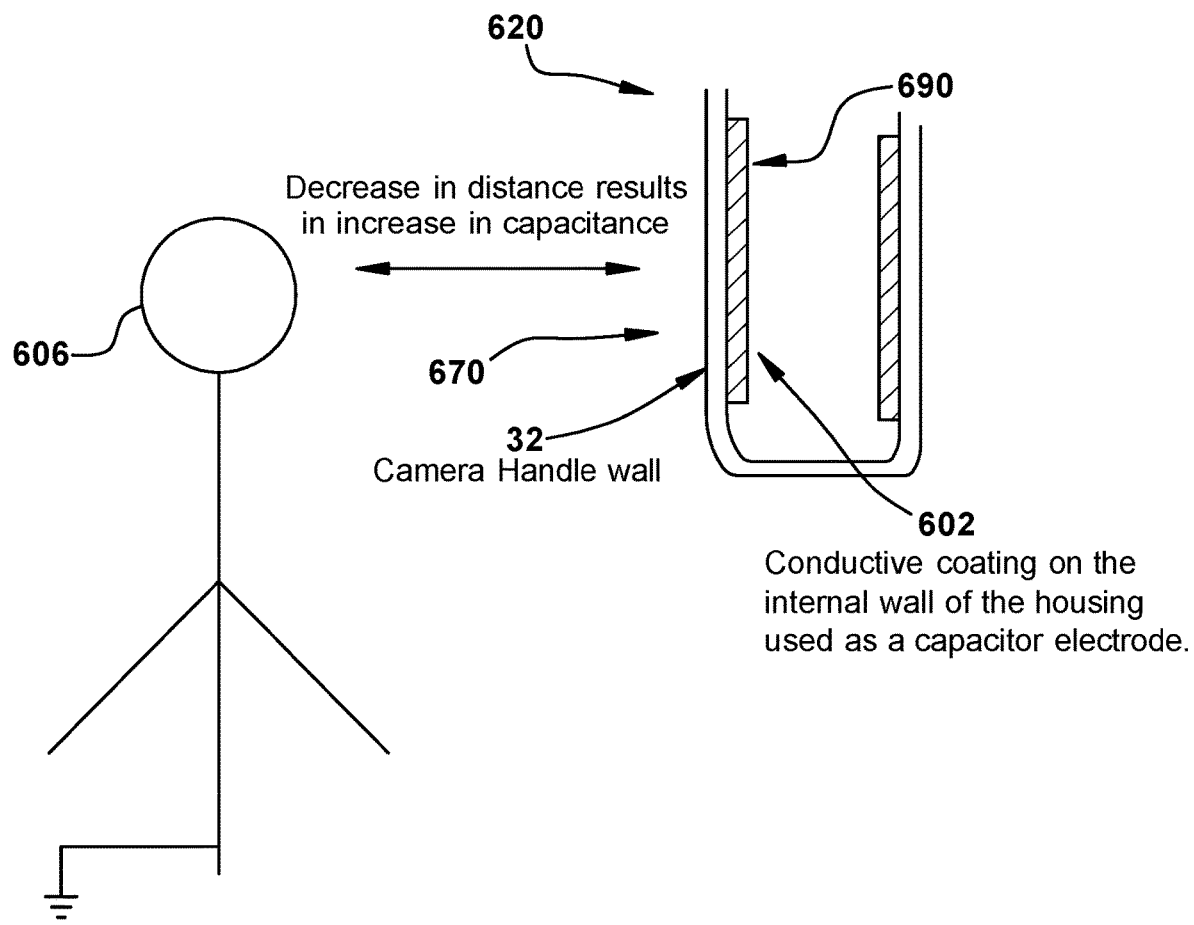
FIG. 11 is a schematic view of on the left side thereof the human body and on the right side thereof a cross section of the handle housing of a handle assembly in accordance with another embodiment of the invention, where an interface device in the form of a capacitive sensor interface section and a conductive coating in the form of a capacitor electrode and respective conductive trace are provided.
Figure 12:
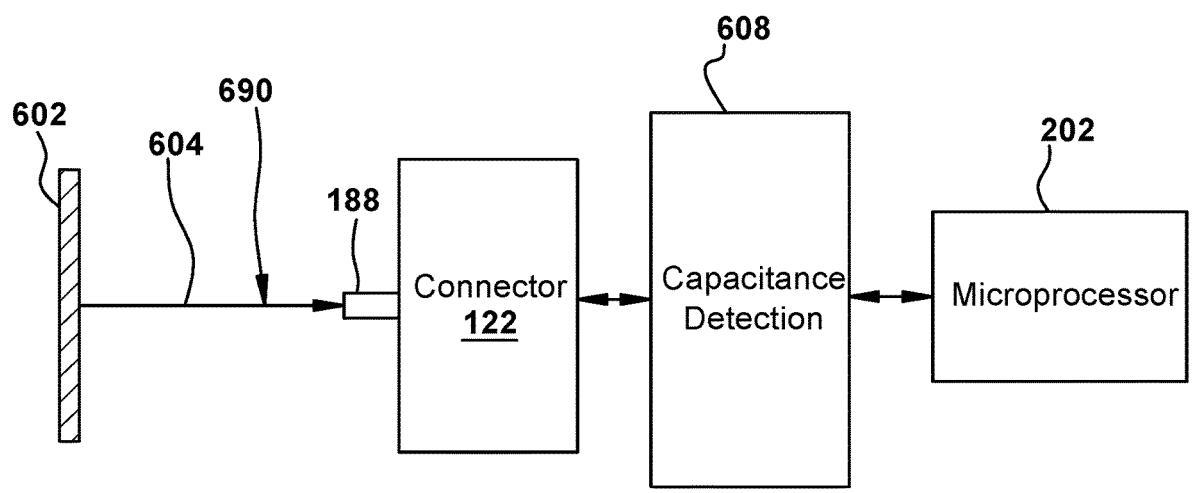
FIG. 12 is a schematic view showing conductive coating of the FIG. 11 handle assembly and a capacitance detection circuit and a processor electrically connected to conductive coating.

FIGS. 11-12 show a handle assembly 620 in accordance with another embodiment of the invention. The FIGS. 11-12 handle assembly 620 is in many respects similar to the above-described handle assemblies 20, 520, and consequently the same reference numerals are used to denote structures corresponding to similar structures in the handle assemblies 20, 520. In addition, the foregoing description of the handle assemblies 20, 520 including the integration into the accessory light head 14 and the medical device support system 10, is equally applicable to the FIGS. 11-12 handle assembly 620 except as noted below. Moreover, it will be appreciated upon reading and understanding the specification that aspects of the handle assemblies 20, 520, 620 may be substituted for one another or used in conjunction with one another where applicable.

The handle assembly 620 includes an interface device 670 in the outer surface 60 of the generally tubular section 44 in the form of a capacitive sensor interface section 670 and a conductive coating 690 on the inner surface 62 of the generally tubular section 44 in the form of a capacitor electrode 602 and conductive trace 604. The capacitor electrode 602 of conductive coating 690 serves as a conductor to form a capacitive interface. More specifically, and with reference to FIG. 11, the human body 606 can be viewed as a ground electrode such that when a corresponding capacitive sensor interface section 670 is within a predetermined distance to the human body 606, a capacitor is formed by a combination of the human body 606 within the predetermined distance to the capacitive sensor interface section 670, the corresponding capacitor electrode 602, and the electrically insulating material of the handle housing 32 there between. As such, the approaching of the human body 606 within the predetermined distance to the capacitive sensor interface section 670, that is from above the capacitor electrode 602, results in a change in capacitance. In some embodiments, the handle assembly 620 may operate as an encroachment indicator wherein the capacitive sensor interface section 670 is configured such that the capacitance in the capacitor increases as the human body 606 approaches the capacitive sensor interface section 670. An exemplary encroachment indicator is described in U.S. Pat. No. 11,039,899, which is incorporated herein by reference. As shown in FIG. 12, the corresponding conductive trace 604 of conductive coating 690 transmits the change in capacitance from the capacitor electrode 602 to the conductive pad 188 to which the connector 122 is connected. The connector 122, in turn, transmits the change in capacitance to a capacitance detection circuit 608 mounted on one of the PCBs 124 for example. The capacitance detection circuit 608 detects the change in capacitance and communicates the detection to the afore described control system 202 for processing.

Figure 13:
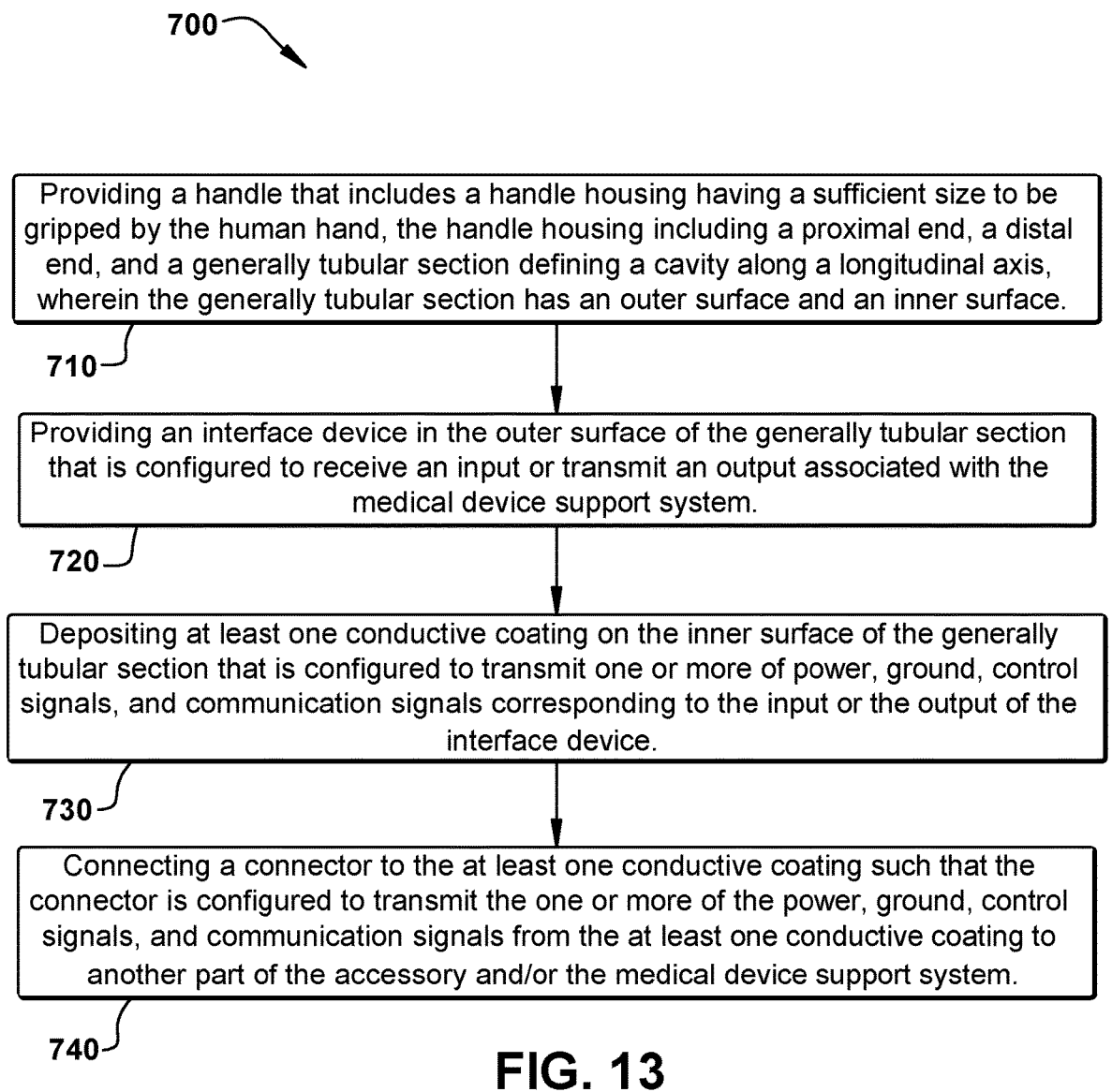
FIG. 13 shows a flowchart of a method in accordance with an embodiment of the invention.

Referring now to FIG. 13, a flowchart 700 is shown of a method of making a handle assembly for an accessory of a medical device support system, such as the handle assemblies 20, 520, 620 for the accessory 14 of the medical device support system 10. Thus, in a step 710, a handle may be provided that includes a handle housing having a sufficient size to be gripped by the human hand, the handle housing including a proximal end, a distal end, and a generally tubular section defining a cavity along a longitudinal axis, wherein the generally tubular section has an outer surface and an inner surface. Step 720 of the method may include providing an interface device in the outer surface of the generally tubular section that is configured to receive an input or transmit an output associated with the medical device support system. Step 730 may include depositing at least one conductive coating on the inner surface of the generally tubular section that is configured to transmit one or more of power, ground, control signals, and communication signals corresponding to the input or the output of the interface device. Step 740 may include connecting a connector to the at least one conductive coating such that the connector is configured to transmit the one or more of the power, ground, control signals, and communication signals from the at least one conductive coating to another part of the accessory and/or the medical device support system.

Although the invention has been shown and described with respect to certain preferred embodiments, it is understood that equivalents and modifications will occur to others skilled in the art upon the reading and understanding of the specification and the attached drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application. The present invention includes all such equivalents and modifications and is limited only by the scope of the following claims.

What is claimed is:

1. A handle assembly for an accessory of a medical device support system, the handle assembly comprising:
   a handle including a handle housing made of an electrically insulating material, the handle having a sufficient size to be gripped by the human hand, the handle housing including a proximal end, a distal end, and a generally tubular section defining an interior region along a longitudinal axis, wherein the generally tubular section has an outer surface and an inner surface;

an interface device in the outer surface of the generally tubular section that is configured to receive an input or transmit an output associated with the medical device support system;

at least one conductive coating on the inner surface of the generally tubular section that is configured to transmit one or more of power, ground, control signals, and communication signals corresponding to the input or the output of the interface device; and, a connector connected to the at least one conductive coating and configured to transmit the one or more of the power, ground, control signals, and communication signals from the at least one conductive coating to another part of the accessory and/or the medical device support system.

2. The handle assembly of claim 1, wherein the interface device includes a pushbutton in the outer surface and the at least one conductive coating includes a positive voltage trace and a button sense trace electrically connected to the pushbutton.

3. The handle assembly of claim 1, wherein the interface device includes a plurality of pushbuttons in the outer surface and the at least one conductive coating includes a positive voltage trace and a button sense trace electrically connected to the pushbuttons in parallel.

4. The handle assembly of claim 1, wherein the interface device includes a light emitting diode (LED) in the outer surface and the at least one conductive coating includes an LED+ drive trace and an LED-return trace electrically connected to the LED.

5. The handle assembly of claim 1, wherein the interface device includes a plurality of light emitting diodes (LEDs) in the outer surface and the at least one conductive coating includes an LED+ drive trace and an LED-return trace electrically connected to the LEDs in parallel.

6. The handle assembly of claim 1, wherein the at least one conductive coating includes a conductive pad and the interface device includes a capacitive touch interface section that are configured such that when the capacitive touch interface section is touched by the human hand a capacitor is formed by the human hand at the capacitive touch interface section, the conductive pad and the electrically insulating material of the handle housing there between.

7. The handle assembly of claim 6, further comprising a capacitance detection circuit configured to detect a change in capacitance in the capacitor when the human hand touches the capacitive touch interface section.

8. The handle assembly of claim 7, wherein the at least one conductive coating includes a conductive trace extending from the conductive pad to the connector, and the connector is configured to transmit the change in capacitance to the capacitance detection circuit.

9. The handle assembly of claim 6, wherein the capacitive touch interface section includes a printed silkscreen in the form of indicia associated with the accessory and/or the medical device support system.

10. The handle assembly of claim 1, wherein the at least one conductive coating includes a capacitor electrode and the interface device includes a capacitive sensor interface section that are configured such that when the human body is within a predetermined distance to the capacitive sensor interface section a capacitor is formed by the human body within the predetermined distance to the capacitive sensor interface section, the capacitor electrode and the electrically insulating material of the handle housing there between.

11. The handle assembly of claim 10, wherein the capacitor is configured such that the capacitance in the capacitor increases as the human body approaches the capacitive sensor interface section.

12. The handle assembly of claim 11, further comprising a capacitance detection circuit configured to detect the change in capacitance in the capacitor as the human body approaches the capacitive sensor interface section.

13. The handle assembly of claim 12, wherein the at least one conductive coating includes a conductive trace extending from the capacitor electrode to the connector, and the connector is configured to transmit the change in capacitance to the capacitance detection circuit.

14. A method of making a handle assembly for an accessory of a medical device support system, the method comprising:

providing a handle including a handle housing having a sufficient size to be gripped by the human hand, the handle housing including a proximal end, a distal end, and a generally tubular section defining a cavity along a longitudinal axis, wherein the generally tubular section has an outer surface and an inner surface;

providing an interface device in the outer surface of the generally tubular section that is configured to receive an input or transmit an output associated with the medical device support system;

depositing at least one conductive coating on the inner surface of the generally tubular section that is configured to transmit one or more of power, ground, control signals, and communication signals corresponding to the input or the output of the interface device; and, connecting a connector to the at least one conductive coating such that the connector is configured to transmit the one or more of the power, ground, control signals, and communication signals from the at least one conductive coating to another part of the accessory and/or the medical device support system.

* * * * *